United States Patent
Bojesen (10) Patent No.: US 10,441,200 B2
(45) Date of Patent: Oct. 15, 2019

(54) AUDIOLOGIC TEST APPARATUS AND METHOD

(71) Applicant: Natus Medical Incorporated, San Carlos, CA (US)

(72) Inventor: Ask Bojesen, Copenhagen (DK)

(73) Assignee: Natus Medical Incorporated, Pleasanton, CA (US)

( * ) Notice: Subject to any disclaimer, the term of this patent is extended or adjusted under 35 U.S.C. 154(b) by 677 days.

(21) Appl. No.: 14/642,552

(22) Filed: Mar. 9, 2015

(65) Prior Publication Data

US 2016/0220155 A1 Aug. 4, 2016

(30) Foreign Application Priority Data

Feb. 4, 2015 (DK) .................................. 2015 70067
Feb. 4, 2015 (EP) ..................................... 15153801

(51) Int. Cl.
*A61B 5/12* (2006.01)
*A61B 5/00* (2006.01)

(52) U.S. Cl.
CPC ............ *A61B 5/126* (2013.01); *A61B 5/0053* (2013.01); *A61B 5/125* (2013.01)

(58) Field of Classification Search
CPC ........ A61B 5/125; A61B 5/126; A61B 5/0053
See application file for complete search history.

(56) References Cited

U.S. PATENT DOCUMENTS 3,757,769 A * 9/1973 Arguimbau ............... A61B 5/12
600/559
2004/0184618 A1 9/2004 Bengtsson
2013/0303941 A1 11/2013 Porges et al.
(Continued)

FOREIGN PATENT DOCUMENTS

WO WO 2014/088578 A1 6/2014

OTHER PUBLICATIONS

First Technical Examination and Search Report dated Sep. 4, 2015, for corresponding Danish Patent Application No. PA 2015 70067, 6 pages.
(Continued)

*Primary Examiner* — Devin B Henson
(74) *Attorney, Agent, or Firm* — Temmerman Law Office; Mathew J. Temmerman Law Office (57) ABSTRACT

An audiologic test apparatus includes: a pump device configured to apply a first pressure to the ear canal; and a processing module for communicatively coupling to the pump device and to a signal generator, wherein the processing module is configured to obtain first acoustic parameter values indicative of an acoustic parameter at the first pressure based on a first broadband signal generated using the signal generator; wherein the pump device is configured to change the first pressure to a changed pressure, and wherein the pump device is also configured to apply a second pressure to the ear canal; and wherein the processing module is also configured to obtain second acoustic parameter values indicative of the acoustic parameter at the second pressure based on a second broadband signal generated using the signal generator, and determine a middle ear resonance frequency based on the first and second acoustic parameter values.

14 Claims, 4 Drawing Sheets

(56) References Cited

U.S. PATENT DOCUMENTS

2014/0296739 A1\* 10/2014 Saltykov ............... A61B 5/125
  600/559
2015/0073297 A1\* 3/2015 Killion ................. A61B 5/6844
  600/559

OTHER PUBLICATIONS

Y. Uchida et al., "Distortion product optoacoustic emission and tympanometric measurements in an adult population-based study", Auris Nasus Larynx, Dec. 2006, vol. 33, Issue 4, 5 pages.
Extended European Search Report dated Jul. 17, 2015, for corresponding EP Patent Application No. 15153801.4, 8 pages.
Murakoshi, et al., "Dynamic characteristics of the middle ear in neonates", International Journal of Pediatric Otorhinolaryngology, Elsevier, Amsterdam, NL, vol. 77, No. 4, Jan. 9, 2013, 9 pages.
Margoklis, et al., "Wideband reflectance tympanometry in normal adults", The Journal of the Acoustical Society of America, American Institute of Physics for the Acoustical Society of America, New York, NY, US, vol. 106, No. 1, Jul. 1, 1999, 16 pages.
Iacovou, et al., "Multi-Frequency Tympanometry: Clinical Applications for the Assessment of the Middle Ear Status", Indian Journal of Otolaryngology and Head & Neck Surgery, vol. 65, No. 3, Jan. 6, 2012, 5 pages.

\* cited by examiner

AUDIOLOGIC TEST APPARATUS AND METHOD

RELATED APPLICATION DATA

This application claims priority to and the benefit of Danish Patent Application No. PA 2015 70067, filed Feb. 4, 2015, pending, and European Patent Application No. 15153801.4, filed Feb. 4, 2015, pending. The entire disclosures of both of the above applications are expressly incorporated by reference herein.

FIELD

The present disclosure relates to an audiologic test apparatus and related method, in particular for performing tympanometry in an ear canal of a subject. In particular, an audiologic test apparatus and related method for measuring one or more ear parameters, including resonance frequency of the middle ear is disclosed.

BACKGROUND

Audiologic tests, such as tympanometry, examines the condition of the middle ear, mobility of the tympanic membrane, and/or the conduction bones by creating variations of pressure in the ear canal. In order to modify the pressure, a probe is inserted into the ear canal creating an air tight seal of the ear canal.

Audiologic tests are conventionally performed by transmitting a continuous tone with a primary component at a primary frequency of 226 Hz towards the tympanic membrane and measuring via a microphone the signal reflected by the tympanic membrane. The choice of 226 Hz is a de facto standard in performing a tympanometry to obtain a tympanogram in adults. In small children a tympanometry is occasionally performed with a tone with a primary component at a primary frequency about 1,000 Hz.

Recent developments within tympanometry include performing a complex and time-consuming test including sequential measurements at many frequencies.

Using a wide-band signal throughout the entire pressure sweep has been proposed. However, such approach leads to superfluous data and reduced signal-to-noise ratio compared to a single-tone signal.

Further, the new approach is not regarded as a standard by authorities, audiologists and other medical personnel.

SUMMARY

Despite the known solutions there is still a need for an improved audiologic test apparatus that provides an accurate tympanometry with short test time.

An audiologic test apparatus is disclosed, the apparatus comprising a pump device for fluidic communication with an ear canal of a subject, wherein the pump device is configured to apply a first pressure to the ear canal; a signal generator; and a processing module for communicatively coupling to the pump device and the signal generator. The processing module is configured to obtain first acoustic parameter values indicative of an acoustic parameter at the first pressure based on a first broadband signal generated using the signal generator, and the pump device is optionally configured to change the pressure in the ear canal from the first pressure to a second pressure, e.g. during first tone signal generation. The pump device is configured to apply a third pressure to the ear canal. The signal generator is optionally configured to generate a first tone signal during the pressure change from the first pressure to the second pressure and/or a third broadband signal at the third pressure. The processing module is configured to obtain third acoustic parameter values indicative of the acoustic parameter at the third pressure based on the third broadband signal generated using the signal generator, and determine a middle ear resonance frequency and/or other ear characteristic, e.g. based on the first acoustic parameter values and/or the third acoustic parameter values.

Also disclosed is a method for performing an audiologic test, the method comprising applying a first pressure to an ear canal of a subject; obtaining first acoustic parameter values of an acoustic parameter at the first pressure based on a first broadband signal; applying a third pressure to the ear canal; obtaining third acoustic parameter values of the acoustic parameter at the third pressure based on a third broadband signal; and optionally determining a middle ear resonance frequency and/or other ear characteristic, e.g. based on the first acoustic parameter values and/or the third acoustic parameter values.

It is an advantage of the present disclosure that a fast and effective test procedure is provided for measuring one or more ear characteristics or ear parameters, including a resonance frequency of the middle ear.

The present method and apparatus provide an audiologic test with reduced wear on the pump device and at the same time optimize the amount of data collected.

Further, a method and apparatus for performing a standard audiologic test is provided.

Advantageously, the method and apparatus provides a first tympanogram with a large signal-to-noise ratio and high pressure resolution, leading to accurate measurements due to high test signal quality.

It is an important advantage of the present disclosure that the risk of triggering the stapedius acoustic reflex may be reduced when compared to using wideband signal tympanometry.

An audiologic test apparatus includes: a pump device for fluidic communication with an ear canal of a subject, wherein the pump device is configured to apply a first pressure to the ear canal; a signal generator; and a processing module for communicatively coupling to the pump device and the signal generator, wherein the processing module is configured to obtain first acoustic parameter values indicative of an acoustic parameter at the first pressure based on a first broadband signal generated using the signal generator; wherein the pump device is configured to change the pressure in the ear canal from the first pressure to a second pressure, and apply a third pressure to the ear canal; wherein the signal generator is configured to generate a first tone signal during the pressure change from the first pressure to the second pressure; and wherein the processing module is configured to obtain third acoustic parameter values indicative of the acoustic parameter at the third pressure based on a third broadband signal generated using the signal generator, and determine a middle ear resonance frequency based on the first acoustic parameter values and the third acoustic parameter values.

Optionally, the processing module is configured to determine a first tympanogram based on the first tone signal generated using the signal generator, and wherein the processing module is configured to determine the third pressure based on the first tympanogram, the third pressure being between the first pressure and the second pressure.

Optionally, wherein the audiologic test apparatus is configured to obtain second acoustic parameter values indicative of the acoustic parameter at the second pressure based on a second broadband signal, and wherein the middle ear resonance frequency is based on the second acoustic parameter values.

Optionally, the processing module is configured to determine a second tympanogram, e.g. based on a second tone signal generated using the signal generator.

Optionally, the second tone signal comprises a second primary component at a second primary frequency corresponding to the middle ear resonance frequency.

Optionally, the first pressure is anywhere from −450 to −150 daPa, and/or the second pressure is anywhere from 150 to 450 daPa.

Optionally, the first pressure is anywhere from 150 to 450 daPa, and/or the second pressure is anywhere from −450 to −150 daPa.

Optionally, the first tone signal comprises a first primary component at a first primary frequency anywhere from 200 to 1,100 Hz.

Optionally, the first broadband signal comprises a plurality of components at different frequencies.

Optionally, the second broadband signal and/or the third broadband signal comprises a plurality of components at different frequencies.

Optionally, the plurality of components have respective frequencies anywhere from 200 Hz to 2000 Hz.

A method for performing an audiologic test includes: applying a first pressure to an ear canal of a subject; obtaining first acoustic parameter values of an acoustic parameter at the first pressure based on a first broadband signal; applying a third pressure to the ear canal; obtaining third acoustic parameter values of the acoustic parameter at the third pressure based on a third broadband signal; and determining a middle ear resonance frequency based on the first acoustic parameter values and the third acoustic parameter values.

Optionally, the method further includes: determining a first tympanogram by generating a first tone signal and varying the pressure in the ear canal from the first pressure to a second pressure; and determining the third pressure based on the first tympanogram.

Optionally, the method further includes obtaining second acoustic parameter values of the acoustic parameter at the second pressure based on a second broadband signal, and wherein the middle ear resonance frequency is based on the second acoustic parameter values.

Other features, embodiments, and advantageous will be described below in the detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

The audiologic test apparatus comprises a processing module, e.g. comprising a microprocessor, an analogue-to-digital converter (ADC), and/or a memory module. The audiologic test apparatus may comprise a housing, e.g. enclosing one or more components of the audiologic test apparatus, e.g. the processing module and/or the pump device. The audiologic test apparatus may comprise one or more interfaces, such as a probe interface and/or a user interface, for communication between components enclosed in the housing and components and/or users external to the audiologic test apparatus. The housing may be a metal housing, a plastic housing, a carbon-fiber-based housing such as a carbon-fiber reinforced polymer or any other material suitable for said housing. In an exemplary apparatus, the housing may be any combination of a metal and plastic and carbon-fiber-based housing.

The processing module may be configured to perform signal analysis on one or more input signals, such as on obtained first acoustic parameter values and/or third acoustic parameter values of one or more acoustic parameters.

The processing module may be configured to provide one or more output signals, such as control signals. The processing module may provide one or more control signals to the signal generator, such as a first and/or a second signal generator control signal. The processing module may provide one or more control signals to the pump device, such as a first and/or a second pump control signal.

The audiologic test apparatus may comprise a pump device connected to the processing module. The pump device may have a port in fluid communication with a pump port of the probe interface, e.g. via a tube or fluid channel. The audiologic test apparatus, e.g. the pump device, may comprise a pressure sensor. The pressure sensor may be configured to measure the actual pressure in the ear canal. The pump device applies different pressures to the ear canal. The first pressure, the second pressure and third pressure are pressures relative to ambient pressure. Thus a first pressure of e.g. −200 daPa indicates a pressure difference between the pressure in the ear canal and ambient pressure, which is known to the skilled person.

The audiologic test apparatus may comprise a microphone and/or the audiologic test apparatus may be configured for connection to a probe microphone of a probe.

The audiologic test apparatus may comprise a signal generator and/or the audiologic test apparatus may be configured for connection to a signal generator of a probe. The signal generator may be configured to generate one or more electrical tests signals, for example including one or more broadband signals and/or one or more tone signals.

The one or more broadband signals include the first broadband signal and optionally the third broadband signal. The one or more broadband signals may include a second broadband signal. The one or more broadband signals include the first broadband signal and optionally the third broadband signal. A broadband signal may be characterized by comprising a plurality of components, such as at least 10, at least 15, at least 20 or at least 30 components, at a respective plurality of different frequencies. Each of the components or at least ten components of the broadband signal components may contain less than 10% of the broadband signal power at the respective frequency or within ±5 Hz of the respective frequency. The components may be sequential, i.e. separated in time, or at least partly overlapping in time. A broadband signal may be a broadband signal. A broadband signal, such as the first broadband signal, the second broadband signal and/or the third broadband, may comprise a primary component in a first frequency range, a secondary component in a second frequency range different from the first frequency range and a tertiary component in a third frequency range different from the first and second frequency ranges.

The one or more tone signals include the first tone signal. The one or more tone signals may include a second tone signal and/or a third tone signal. A tone signal may be characterized by having a primary component at a primary frequency, e.g. centered around or at a first primary frequency. In an exemplary tone signal, the primary component contains at least 80% of the tone signal power at the primary frequency or within ±5 Hz of the primary frequency. In an exemplary tone signal with a primary and secondary component at respective primary and secondary frequencies, the primary component contains at least 40% of the tone signal power at the primary frequency or within ±5 Hz of the primary frequency and/or the secondary component contains at least 40% of the tone signal power at the secondary frequency or within ±5 Hz of the secondary frequency. The first tone signal and/or the second signal may be a pure tone signal or substantially a pure tone signal, e.g. a signal consisting of a single component or substantially a single component.

A user interface of the audiologic test apparatus may comprise a display, such as an LCD display, an LED display, an OLED display. The display enables audiologic test apparatus to provide test results, e.g. in the form of test curves or test values to a practician of the audiologic test apparatus.

The signal generator may be configured for connection to one or more speakers, such as one or more probe speakers via a probe interface and/or one or more speakers arranged in the housing of the audiologic test apparatus.

The audiologic test apparatus may comprise a probe interface. The probe interface may provide connection to a probe. The probe interface may comprise one or more electrical connectors and/or one or more fluid communication channels, such as a pump port. The one or more electrical connectors may provide electrical connection between components of the audiologic test apparatus and components of the probe. For example, the electrical connectors may provide electrical connection between the signal generator and a probe speaker, e.g. for feeding test signals to the probe. The electrical connectors may provide electrical connection between the processing module and a probe microphone, e.g. for feeding measurement signal(s) indicative of acoustic parameter values to the processing module. The one or more fluid communication channels and/or pump ports may provide fluid communication between a probe and the pump device of the audiologic test apparatus, e.g. in order to adjust pressure in the ear canal of a test person during a test procedure.

The audiologic test apparatus is configured to obtain first acoustic parameter values or data of an acoustic parameter, e.g. by receiving a microphone signal, such as a probe microphone signal or a microphone signal from a microphone arranged in the audiologic test apparatus and communicatively coupled to the ear canal.

Acoustic parameter values are data samples of a microphone or other sensor output.

The acoustic parameter may be the complex admittance or conductance of the middle ear, or at least a part thereof, e.g. real part, imaginary part, absolute value and/or argument/phase.

The audiologic test apparatus is configured to apply a first pressure, such as a positive pressure $P_+$ or a negative pressure $P_-$, to the ear canal by the pump device, e.g. by sending a pump control signal from the processing module to the pump device. The first pressure may be in the range from −450 to −150 daPa or in the range from 150 to 450 daPa. The first pressure may be a pressure extreme for the audiologic test.

The processing module may be configured to determine a first tympanogram based on the first tone signal generated using the signal generator. The processing module may be configured to determine the third pressure based on the first tympanogram. The third pressure may be between the first pressure and the second pressure. The audiologic test apparatus may be configured to obtain second acoustic parameter values indicative of the acoustic parameter at the second pressure based on a second broadband signal. The middle ear resonance frequency may be based on the second acoustic parameter values. The processing module may be configured to determine a second tympanogram based on a second tone signal generated using the signal generator.

Optionally, the audiologic test apparatus is configured to generate a first tone signal to the ear canal with the signal generator and to vary the pressure in the ear canal from the first pressure to a second pressure with the pump device, e.g. during generation of the first tone signal. The first tone signal may comprise a first primary component at a first primary frequency in the range from 200 to 1,100 Hz. The first tone signal may comprise a first primary component at a first primary frequency in the range from 210 to 240 Hz, such as about 226 Hz, in the range from 650 to 700 Hz, such as about 678 Hz, in the range from 775 to 825 Hz, such as about 800, or in the range from 950 to 1,050 Hz, such as about 1,000 Hz. The second pressure may be a positive pressure $P_+$ if the first pressure is a negative pressure $P_-$ or a negative pressure $P_-$ if the first pressure is a positive pressure $P_+$. The second pressure may be in the range from −450 to −150 daPa or in the range from 150 to 450 daPa. In exemplary apparatus, the first pressure and/or the second pressure may be less than −450 daPA, such as about −600 daPa. In exemplary apparatus, the first pressure and/or the second pressure may be larger than 450 daPa, such as about 600 daPa. The audiologic test apparatus may be configured to obtain second acoustic parameter values of an acoustic parameter at the second pressure, e.g. by generating a second broadband signal. The middle ear resonance frequency may be based on the second acoustic parameter values.

The audiologic test apparatus is configured to apply a third pressure to the ear canal with the pump device. The third pressure may be ambient pressure $P_0$. The third pressure may be a tympanic peak pressure $P_{TPP}$. The tympanic peak pressure may also be denoted TPP The processing module may be configured to determine a first tympanogram based on generation of the first tone signal, and optionally the processing module is configured to determine the third pressure based on the first tympanogram, e.g. by selecting $P_{TPP}$ as the third pressure. The third pressure may be between the first pressure and the second pressure.

The audiologic test apparatus is configured to determine a middle ear resonance frequency $f_{Res}$ based on the first acoustic parameter values and/or the third acoustic parameter values. The middle ear resonance frequency may be determined using the so-called Vanhuyse Model, where the middle ear resonant frequency $f_{RES}$ is determined indirectly, by measuring/determining:

1. $P_{TPP}$ (Tympanometric Peak Pressure)
a. This pressure is close to ambient pressure for normal ears.
b. The ambient pressure $P_0$ may be used instead of $P_{TPP}$ for determining the middle ear resonant frequency.
2. The complex admittance Y(f) as a function of probe frequency f at pressure extreme (first pressure).
a. The frequency range for f may be from 200 Hz to 2,500 Hz
b. Pressure extreme is in the negative range $P_-=-400$ to $-200$ daPa and/or in the positive range $P_+=200$ to 400 daPa
3. The complex admittance Y(f) as a function of probe frequency f at $P_{TPP}$ or $P_0$ (third pressure)
a. The frequency range for f may be from 200 Hz to 2,000 Hz Determining a middle ear resonance frequency based on the first acoustic parameter values and the third acoustic parameter values (sample values indicative of complex admittance at first pressure and third pressure, respectively) may comprise calculating the difference of the complex admittance:

$$\Delta Y(f) = Y(f, P=P_{TPP} \text{ or } P_0) - Y(f, P=P_\pm)$$

$\Delta Y(f)$ may be denoted the peak compensated static acoustic admittance or baseline compensated admittance.

The middle ear resonance frequency $f_{RES}$ may now be identified as the frequency where the phase of $\Delta Y(f)$ is zero. Accordingly, plotting the phase of $\Delta Y(f)$ as a function of frequency reveals the middle ear resonance frequency $f_{RES}$ as the frequency where the phase crosses zero, see FIG. 4.

The audiologic test apparatus may be configured to determine a second tympanogram by generating a second tone signal. The second tone signal may comprise a second primary component at a second primary frequency corresponding to the middle ear resonance frequency.

A broadband signal, such as the first broadband signal and/or the third broadband signal, and optionally the second broadband signal may comprise a plurality of components at different frequencies. The plurality of components may have respective frequencies anywhere from 200 Hz to 2000 Hz. The plurality of frequencies may be selected at frequencies in a frequency range from 200 Hz to 2,000 Hz. A first frequency of the plurality of frequencies may be in the range from 200 to 500 Hz and a second frequency of the plurality of frequencies may be in the range from 500 to 2,000 Hz.

The method may comprise determining a first tympanogram by generating a first tone signal and varying the pressure in the ear canal from the first pressure to a second pressure. In the method, determining the third pressure may be based on the first tympanogram.

The method may comprise obtaining second acoustic parameter values of an acoustic parameter at the second pressure by generating a second broadband signal, and the middle ear resonance frequency may be based on the second acoustic parameter values. This allows for a more accurate determination of the middle ear resonance frequency without introducing further wear on the pump device.

Figure 1:
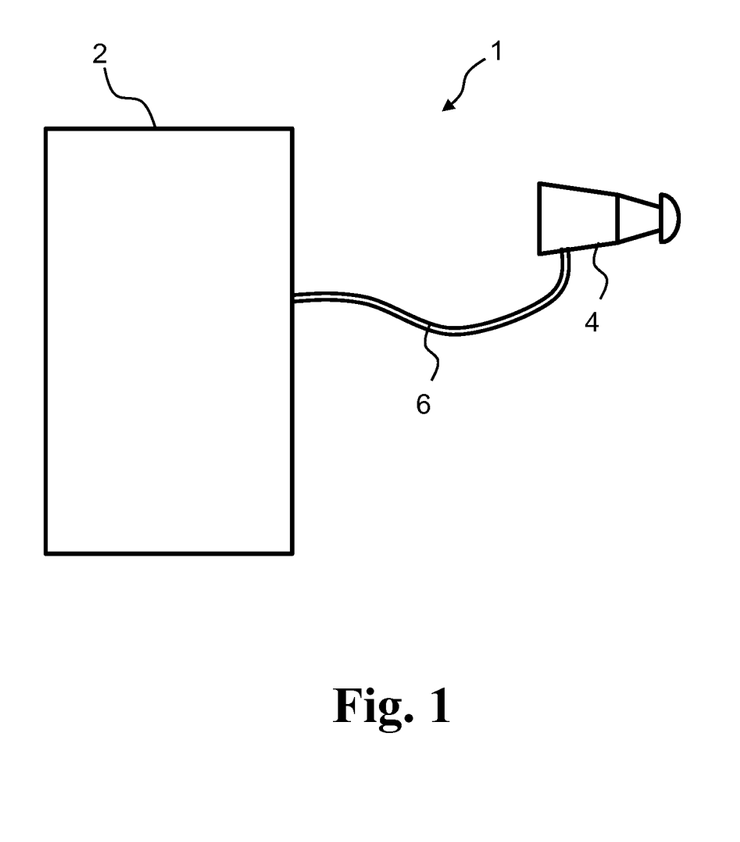
FIG. 1 schematically illustrates an exemplary audiologic test system comprising an audiologic test apparatus, FIG. 2 schematically illustrates an exemplary audiologic test apparatus.

FIG. 1 schematically illustrates an exemplary audiologic test system 1 for performing an audiologic test. The audiologic test system 1 comprises an audiologic test apparatus 2 and a test probe 4. A probe cable 6 connects the test probe 4 to the audiologic test apparatus 2.

Figure 2:
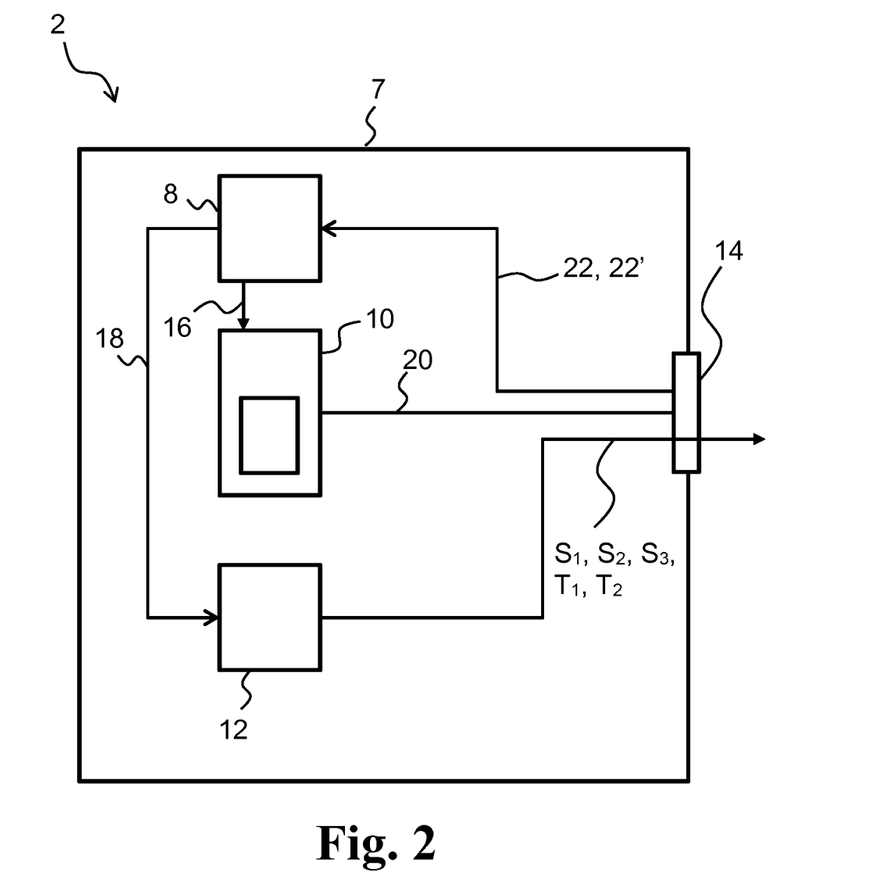

FIG. 2 schematically illustrates an exemplary audiologic test apparatus. The audiologic test apparatus 2 comprises a housing 7, a processing module 8, a pump device 10, a signal generator 12 and probe interface 14. The processing module 8 is connected to the pump device 10 and the signal generator 12 and controls the pump device 10 and the signal generator 12 with respective pump control signal(s) 16 and signal generator control signal 18. The pump device 12 is connected to a pump port (not shown) of the probe interface 14 via fluid connection 20 and applies a pressure to the pump port according to a pump control signal from the processing module 8. During use, a probe is connected to the pump port such that the pressure applied to the pump port by the pump device is applied to the ear canal. Thus, the audiologic test apparatus 2 is configured to apply a first pressure to the ear canal by the pump device 10.

The processing module 8 is connected to electrical connector(s) of the probe interface and obtains or measures (first) acoustic parameter values 22 indicative of acoustic admittance from a microphone or other sensor element of a probe via probe interface 14, when the pump device 10 applies the first pressure according to pump control signal 16 from the processing module 8 and the signal generator 12 generates a first broadband signal $S_1$ according to signal generator control signal 16 from the processing module 8. After generation of the first broadband signal at the first pressure, the processing module 8 controls the signal generator 12 to generate a first tone signal $T_1$ to the ear canal, and the pump device 10 to vary the pressure in the ear canal from the first pressure to a second pressure. Subsequently, the processing module 8 controls the pump device 10 to apply a third pressure to the ear canal. At the third pressure, the processing module 8 controls signal generator 12 to generate a third broadband signal $S_3$ and obtains (third) acoustic parameter values 22' indicative of acoustic admittance. Upon measuring third acoustic parameter values indicative of acoustic admittance, the processing module 8 determines a middle ear resonance frequency based on the first acoustic parameter values and the third acoustic parameter values by determining the baseline compensated admittance and identifying the middle ear resonance frequency as the frequency where the phase of the baseline compensated admittance is zero. The middle ear resonance frequency may be shown on a display (not shown), sent to a printing device, and/or saved in an electronic patient file.

Figure 3:
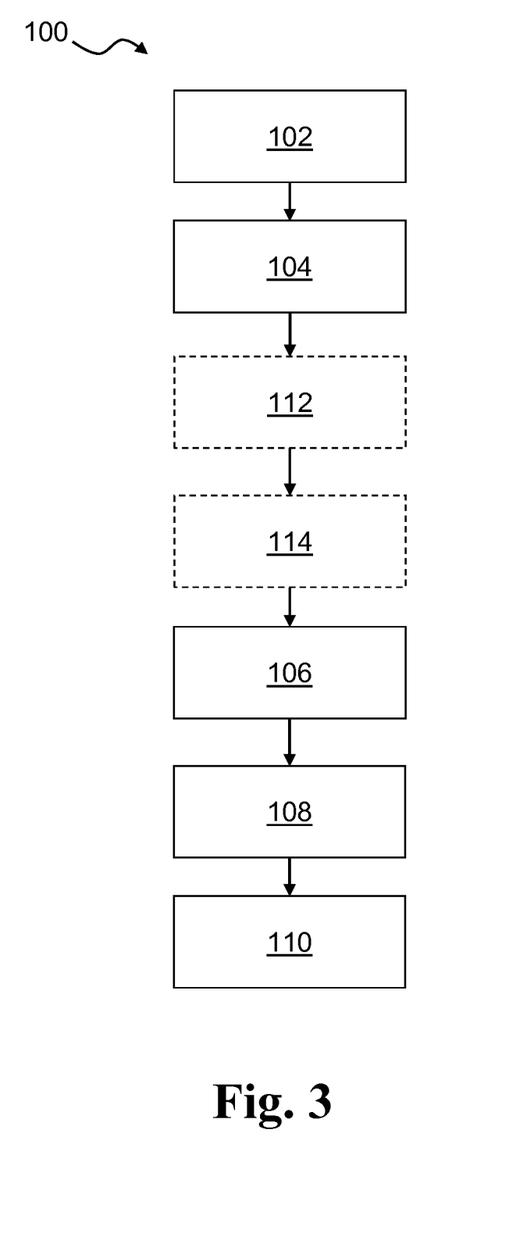
FIG. 3 is a flow diagram of an exemplary method.

FIG. 3 is a flow diagram of a method 100 for performing an audiologic test. The method comprises applying 102 a first pressure to an ear canal of a subject; obtaining 104 first acoustic parameter values of an acoustic parameter at the first pressure by generating a first broadband signal. Then, the method proceeds to applying 106 a third pressure to the ear canal, obtaining 108 third acoustic parameter values of the acoustic parameter at the third pressure by generating a third broadband signal; and determining 110 a middle ear resonance frequency based on the first acoustic parameter values and the third acoustic parameter values. Optionally as indicated with the dotted box, the method 100 may comprise determining 112 a first tympanogram by generating a first tone signal and varying the pressure in the ear canal from the first pressure to a second pressure and determining the third pressure based on the first tympanogram. Optionally as indicated with the dotted box, the method may comprise obtaining 114 second acoustic parameter values of an acoustic parameter at the second pressure by generating a second broadband signal. Determining 110 the middle ear resonance frequency may be based on the second acoustic parameter values obtained in 114.

Figure 4:
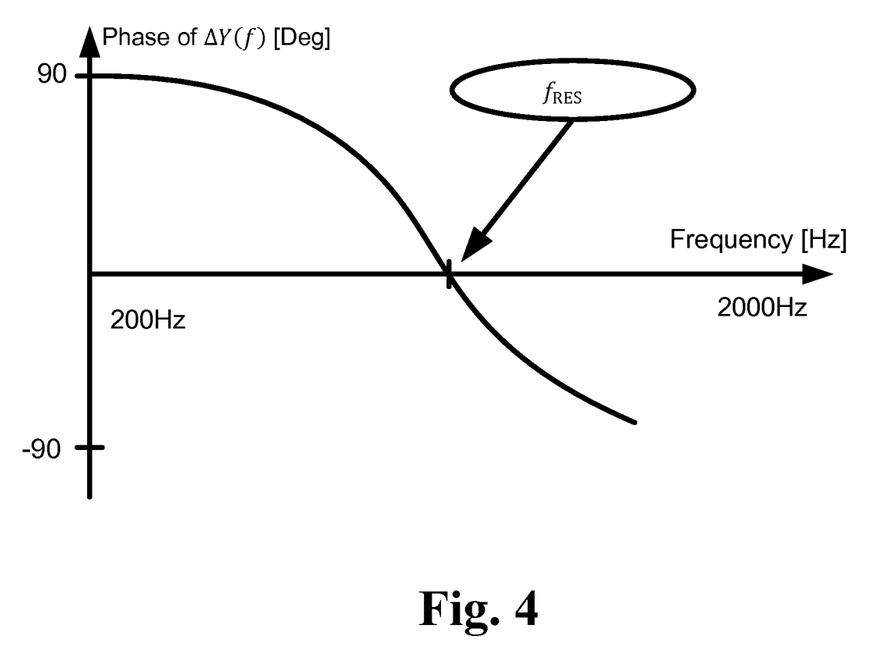
FIG. 4 is a graph illustrating determination of the middle ear resonance frequency.

FIG. 4 is a graph showing the phase of $\Delta Y(f)$ as a function of frequency. The middle ear resonance frequency is identified as the frequency where the phase crosses zero, i.e. where the phase of $\Delta Y(f)$ is zero.

Exemplary methods are also disclosed in the following examples.

Example 1 (Negative Pressure Sweep, $P_{TPP}$ or Ambient Pressure)

1. Apply first pressure (e.g. $P_+=200$ daPa) and obtain/measure complex admittance $Y(f, P_+)$ using a first broadband signal $S_1$.
2. Make a first tympanogram with first tone signal $T_1$ (e.g. at 226 Hz) from first pressure $(P_+)$ to second pressure $(P_-)$.
3. Optional: Measure the complex admittance $Y(f, P_-)$ at the second pressure using a second broadband signal $S_2$.
4. Apply third pressure (e.g. $P_{TTP}$ derived from first tympanogram or ambient pressure) and obtain/measure the complex admittance $Y(f, P_{TPP}$ or $P_{def})$ using a third broadband signal $S_3$.
5. Determine a middle ear resonance frequency $f_{RES}$ based on the complex admittances measured at the first and third pressures.
6. Optional: Make a second tympanogram with a second tone signal $T_2$ having a primary component at the middle ear resonant frequency $f_{RES}$: $Y(f_{RES}, P)$.

Pressure applied during this sequence: $P_0 \rightarrow P_+ \rightarrow P_- \rightarrow P_{TPP} \rightarrow P_0$, or $P_0 \rightarrow P_+ \rightarrow P_- \rightarrow P_0$, where $P_0$ is relative pressure to the surroundings.

Example 2 (Positive Pressure Sweep, $P_{TPP}$ or Ambient Pressure)

1. Apply first pressure $P_-$ (e.g. $P_-=-400$ daPa) and obtain/measure complex admittance $Y(f, P_-)$ using a first broadband signal $S_1$.
2. Make a first tympanogram with first tone signal $T_1$ (e.g. at 226 Hz) from first pressure $(P_-)$ to second pressure $(P_+)$.
3. Optional: Measure the complex admittance $Y(f, P_+)$ using a second broadband signal $S_2$.
4. Apply third pressure (e.g. $P_{TTP}$ derived from first tympanogram or ambient pressure) and obtain/measure the complex admittance $Y(f, P_{TPP}$ or $P_{def})$ using a third broadband signal $S_3$.
5. Determine a middle ear resonance frequency $f_{RES}$ based on the complex admittances measured at the first and third pressures.
6. Optional: Make a second tympanogram with a second tone signal $T_2$ having a primary component at the middle ear resonant frequency $f_{RES}$: $Y(f_{RES}, P)$.

Pressure applied during this sequence: $P_0 \rightarrow P_- \rightarrow P_+ \rightarrow P_{TPP} \rightarrow P_0$, or $P_0 \rightarrow P_- \rightarrow P_+ \rightarrow P_0$, where $P_0$ is relative pressure to the surroundings.

The use of the terms "first", "second", "third" and the like does not imply any particular order, but they are included to identify individual elements. Moreover, the use of the terms first, second, etc. does not denote any order or importance, but rather the terms first, second, third, etc. are used to distinguish one element from another. Note that the words first, second and third are used here and elsewhere for labelling purposes only and are not intended to denote any specific spatial or temporal ordering unless otherwise stated. Furthermore, the labelling of a third element does not imply the presence of a second element or vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES

1 audiologic test system
2 audiologic test apparatus
4 test probe
6 probe cable
7 housing
8 processing module
10 pump device
12 signal generator
14 probe interface
16 pump control signal
18 signal generator control signal
20 fluid connection
22 first acoustic parameter values
22' third acoustic parameter values
100 method for performing an audiologic test
102 applying a first pressure
104 obtaining first acoustic parameter values
106 applying a third pressure
108 obtaining third acoustic parameter values
110 determining middle ear resonance frequency
112 determining a first tympanogram and determining the third pressure based on the first tympanogram
114 obtaining second acoustic parameter values
$S_1$ first broadband signal
$S_2$ second broadband signal
$S_3$ third broadband signal
$T_1$ first tone signal
$T_2$ second tone signal

The invention claimed is:

1. An audiologic test apparatus comprising:
a pump device for fluidic communication with an ear canal of a subject, the pump device configured to apply a first pressure to the ear canal, change the pressure in the ear canal from the first pressure to a second pressure and apply a third pressure to the ear canal;
a signal generator configured to generate a first tone signal during the pressure change from the first pressure to the second pressure; and
a processing module for communicatively coupling to the pump device and the signal generator, the processing module configured to obtain first acoustic parameter values indicative of an acoustic parameter at the first pressure based on a first broadband signal generated using the signal generator, second acoustic parameter values indicative of the acoustic parameter at the second pressure based on a second broadband signal using the signal generator and third acoustic parameter values indicative of the acoustic parameter at the third pressure based on a third broadband signal generated using the signal generator;

whereby the processing module determines a middle ear resonance frequency from a baseline compensated admittance based on the first acoustic parameter values and the third acoustic parameter values; and wherein the processing module is configured to determine a first tympanogram based only on the first tone signal generated using the signal generator, and wherein the processing module is configured to determine the third pressure based only on the first tympanogram, the third pressure being between the first pressure and the second pressure.

2. The audiologic test apparatus according to claim 1, wherein the middle ear resonance frequency is based on the second acoustic parameter values.

3. The audiologic test apparatus according to claim 1, wherein the processing module is configured to determine a second tympanogram based on a second tone signal generated using the signal generator.

4. The audiologic test apparatus according to claim 3, wherein the second tone signal consists of a second primary component at a second primary frequency corresponding to the middle ear resonance frequency.

5. The audiologic test apparatus according to claim 1, wherein the first pressure is anywhere from −450 to −150 daPa, and the second pressure is anywhere from 150 to 450 daPa.

6. The audiologic test apparatus according to claim 1, wherein the first pressure is anywhere from 150 to 450 daPa, and the second pressure is anywhere from −450 to −150 daPa.

7. The audiologic test apparatus according to claim 1, wherein the first tone signal consists of a first primary component at a first primary frequency anywhere from 200 to 1,100 Hz.

8. The audiologic test apparatus according to claim 1, wherein the first broadband signal consists of a plurality of components at different frequencies.

9. The audiologic test apparatus according claim 8, wherein the plurality of components have respective frequencies anywhere from 200 Hz to 2000 Hz.

10. The audiologic test apparatus according to claim 1, wherein the third broadband signal consists of a plurality of components at different frequencies.

11. The audiologic test apparatus according to claim 1, wherein the baseline compensated admittance is the difference of the complex admittance indicative of the first acoustic parameter values and the third acoustic parameter values.

12. A method for performing an audiologic test, comprising:
applying a first pressure to an ear canal of a subject;
obtaining first acoustic parameter values of an acoustic parameter at the first pressure based on a first broadband signal;
varying the pressure in the ear canal from the first pressure to a second pressure;
determining a first tympanogram only by generating a first tone signal by varying the pressure in the ear canal from the first pressure to the second pressure;
obtaining second acoustic parameter values of the acoustic parameter at the second pressure based on a second broadband signal;
applying a third pressure to the ear canal, the third pressure being determined based only on the first tympanogram, and the third pressure being between the first pressure and the second pressure;
obtaining third acoustic parameter values of the acoustic parameter at the third pressure based on a third broadband signal; and
determining a middle ear resonance frequency from a baseline compensated admittance based on the first acoustic parameter values and the third acoustic parameter values.

13. The method according to claim 12, wherein the middle ear resonance frequency is based on the second acoustic parameter values.

14. The method of claim 12, wherein the baseline compensated admittance is the difference of the complex admittance indicative of the first acoustic parameter values and the third acoustic parameter values.

* * * * *